United States Patent
Medina Malaver

(10) Patent No.: US 8,428,723 B2
(45) Date of Patent: Apr. 23, 2013

(54) EXTERNAL COIL ASSEMBLY FOR A TRANSCUTANEOUS SYSTEM

(75) Inventor: Evelia Ysabel Medina Malaver, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 1811 days.

(21) Appl. No.: 11/214,908

(22) Filed: Aug. 31, 2005

(65) Prior Publication Data
US 2006/0030905 A1  Feb. 9, 2006

Related U.S. Application Data

(63) Continuation-in-part of application No. 29/206,716, filed on Jun. 3, 2004, now Pat. No. Des. 512,416.

(51) Int. Cl.
*A61N 1/00* (2006.01)
(52) U.S. Cl.
USPC ............................................. 607/33
(58) Field of Classification Search ...................... 607/33
See application file for complete search history.

(56) References Cited

U.S. PATENT DOCUMENTS

| 452,003 | A | 5/1891 | Lipe |
|---|---|---|---|
| 3,043,000 | A | 7/1962 | Hatfield |
| D227,118 | S | 6/1973 | Muraoka |
| 3,771,685 | A | 11/1973 | Micallef |
| 4,003,521 | A | 1/1977 | Hess |
| 4,226,164 | A | 10/1980 | Carter |
| 4,240,428 | A | 12/1980 | Akhavi |
| D267,541 | S | 1/1983 | Kanemitsu |
| 4,414,701 | A | 11/1983 | Johnson |
| 4,606,329 | A | 8/1986 | Hough |
| 4,610,621 | A | 9/1986 | Taber et al. |
| 4,726,378 | A | 2/1988 | Kaplan |
| 4,731,718 | A | 3/1988 | Sheu |
| 4,736,747 | A * | 4/1988 | Drake ............................ 607/61 |
| 4,917,504 | A | 4/1990 | Scott et al. |
| 4,920,679 | A | 5/1990 | Sarles et al. |
| 5,014,592 | A | 5/1991 | Zweig et al. |
| D348,067 | S | 6/1994 | Lucey et al. |
| 5,603,726 | A | 2/1997 | Schulman et al. |
| 5,775,652 | A | 7/1998 | Crawshaw et al. |

(Continued)

FOREIGN PATENT DOCUMENTS

| GB | 00414579 A | 8/1934 |
|---|---|---|
| GB | 2 266 045 A | 10/1993 |

OTHER PUBLICATIONS

Rutter, "Comparison: Lightwave 2000,3000,4000, Illuminator and Pocket-Bright, and Petzl Tikka", http://www.dansdata.com/ledlights7.htm, Feb. 14, 2002, 1-30.

*Primary Examiner* — Christopher D Koharski
*Assistant Examiner* — Michael Carey
(74) *Attorney, Agent, or Firm* — Kilpatrick, Townsend & Stockton, LLP.

(57) ABSTRACT

An external coil assembly for a transcutaneous system is disclosed. The assembly comprises: a housing having a skin-adjacent surface, an opposing exposed surface and a threaded shaft open to the exposed surface and extending toward the skin-adjacent surface; an external coil secured within the housing; and a magnet with a threaded exterior surface to threadingly engage the threaded shaft, wherein at least one of either the shaft thread or the magnet thread has at least one transverse channel forming discontinuities in the thread.

32 Claims, 8 Drawing Sheets

U.S. PATENT DOCUMENTS

| | | |
|---|---|---|
| 5,785,477 A | 7/1998 | McGuffey et al. |
| 5,971,334 A | 10/1999 | Crawshaw et al. |
| 6,073,973 A | 6/2000 | Boscaljon et al. |
| 6,244,142 B1 * | 6/2001 | Swanson .................. 81/460 |
| 6,259,951 B1 | 7/2001 | Kuzma et al. |
| 6,272,382 B1 | 8/2001 | Faltys et al. |
| 6,308,101 B1 | 10/2001 | Faltys et al. |
| 6,542,777 B1 | 4/2003 | Griffith et al. |
| 6,571,676 B1 | 6/2003 | Folsom et al. |
| 6,668,065 B2 | 12/2003 | Lee et al. |
| 6,838,963 B2 | 1/2005 | Zimmerling et al. |
| 6,857,612 B2 * | 2/2005 | Goodbred .................. 248/429 |
| 2002/0076071 A1 | 6/2002 | Single |
| 2003/0181956 A1 | 9/2003 | Duncan et al. |
| 2004/0260361 A1 * | 12/2004 | Gibson ..................... 607/57 |
| 2005/0004629 A1 * | 1/2005 | Gibson et al. ............. 607/60 |
| 2008/0009920 A1 | 1/2008 | Gibson et al. |

* cited by examiner

EXTERNAL COIL ASSEMBLY FOR A TRANSCUTANEOUS SYSTEM

CROSS-REFERENCE TO RELATED APPLICATIONS

This application is a continuation-in-part of U.S. patent application Ser. No. 29/206,716, now U.S. Design Pat. No. D512,416, entitled "Magnet Housing for Coil," filed Jun. 3, 2004, which is hereby incorporated by reference herein in its entirety.

BACKGROUND

1. Field of the Invention

The present invention relates generally to transcutaneous systems, and more particularly, to an external coil assembly of an transcutaneous system.

2. Related Art

The use of implantable medical devices to provide therapy to individuals for various medical conditions has become more widespread as the advantages and benefits such devices provide become more widely appreciated and accepted.

Medical devices designed for temporary or permanent implantation include, for example, cardiac assist or replacement devices such as pacemakers, defibrillators, circulatory assist devices and artificial hearts; stimulating devices such as Cochlear™ implants, neuromuscular simulators, bone growth stimulators. etc; biosensors, and others. Most implantable medical devices that perform work (active devices) and many of those that do not (passive devices) require power.

For those that require more power than can reasonably be provided by an implantable energy storage device, power must be transferred to the implanted device during its operational life. Traditionally, a percutaneous lead has been used to effect such power transfer. However, due to the high incidence of infection and other drawbacks, inductively-coupled transcutaneous energy transfer (TET) systems are more commonly utilized to provide the requisite power to an implanted device. Transcutaneous systems have also been utilized to transfer data additionally or alternatively to power.

A variety of arrangements have been developed or proposed for transcutaneous transmission of data or power. For example, in addition to providing power, transcutaneous energy and information transmission (TEIT) systems are used to transfer data utilizing the inductively-coupled coils or a separate, integrated device such as an infra-red (IR) communication device. For example, in some Cochlear™ implants a radio frequency link is established between the coils of a transcutaneous system to transmit encoded stimulus information to an internal receiver that delivers the stimuli to electrodes implanted in the cochlear. These and other systems which include the use of inductively-coupled coils are generally and collectively referred to herein as transcutaneous systems.

Generally, the subcutaneous coil is implanted just beneath the surface of the skin, while the external coil is located on the skin surface in alignment with the implanted coil. Because efficient energy transfer requires the coils to be aligned, various approaches have been developed to maintain such alignment between the external and implanted coils. Such previous approaches include ear hooks, headgear, pegs, VELCRO™, clips, skin pouches, and other mechanical alignment systems. These approaches suffered from poor alignment and increased possibility of infection. More recently, these approaches have been surpassed with the use of attractive magnets fixed relative to the internal and external coils. For example, in Cochlear™ implants, an internal coil and magnet are surgically secured to the cranium while the external coil is held on the scalp in alignment with the implanted coil by a magnet.

SUMMARY

In accordance with one aspect of the present invention, an external coil assembly for a transcutaneous system is disclosed. The assembly comprises: a housing having a skin-adjacent surface, an opposing exposed surface and a threaded shaft open to the exposed surface and extending toward the skin-adjacent surface; an external coil secured within the housing; and a magnet with a threaded exterior surface to threadingly engage the threaded shaft, wherein at least one of either the shaft thread or the magnet thread has at least one transverse channel forming discontinuities in the thread.

In accordance with another aspect of the present invention, a magnet is disclosed. The magnet comprises: an exterior surface having a thread configured to engage a threaded shaft in an external coil assembly of a transcutaneous system, wherein the magnet thread has at least one transverse channel forming discontinuities in the thread.

In accordance with a further aspect of the present invention, an external coil assembly for a transcutaneous system is disclosed. The system comprises: housing means for housing an external coil of a transcutaneous system, the housing means having a skin-adjacent surface, an opposing exposed surface and a threaded shaft open to the exposed surface and extending toward the skin-adjacent surface; and magnet means having a threaded exterior surface for threadingly engaging the threaded shaft, wherein at least one of either the shaft thread or the magnet thread has at least one transverse channel forming discontinuities in the thread.

In accordance with a still further aspect of the present invention, a method for facilitating removal of debris accumulating between a magnet and a housing of an external coil assembly of a transcutaneous system is disclosed. The method comprises: providing at least one transverse channel in the housing; and collecting debris which accumulates between the housing and the magnet in one or more of the at least one transverse channel.

BRIEF DESCRIPTION OF THE DRAWINGS

Embodiments of the present invention will be described in conjunction with the accompanying drawings, in which.

DETAILED DESCRIPTION

The present invention is generally directed to a housing for an external coil of a transcutaneous system. The housing has a skin-adjacent surface, an opposing exposed surface and a threaded shaft open to the exposed surface and extending toward the skin-adjacent surface. An external coil is secured within the housing. A magnet having a threaded exterior surface to threadingly engage the threaded shaft is also provided. In accordance with the teachings of the present invention, either or both the shaft thread or the magnet thread has/have at least one transverse channel forming discontinuities in the thread.

Advantageously, the transverse channel(s) accumulate/s and collect/s debris that may become lodged between neighboring portions of the shaft or magnet threads. This provides for easier adjustment of the magnet in the housing, as well as removal and replacement of the magnet. Also, the channel(s) is/are accessible to the recipient, facilitating removal of the debris by the recipient using, for example, a finger, pen, needle, knife, scissors, or other suitable item. It is noted that the above and additional or alternative embodiments are provided by embodiments of the present invention without compromising the mechanical integrity of the external coil assembly.

There are several types of medical devices that include temporarily- or permanently-implanted components that, when implanted, exchange data or power with external components using a transcutaneous system. Such medical devices include but are not limited to cardiac assist or replacement devices, stimulating devices, biosensors, and the like.

The present invention will be described in conjunction with one such medical device, a prosthetic hearing implant, such as a Freedom™, Nucleus™ or Cochlear™ implants sold by Cochlear Limited. Such devices are described in U.S. Pat. Nos. 4,532,930, 6,537,200, 6,565,503, 6,575,894, and 6,697,674, the entire contents and disclosures of which are hereby incorporated by reference. It should be understood to those skilled in the art that the present invention may be used in transcutaneous systems implemented in any of the above or other implantable medical devices.

Figure 1:
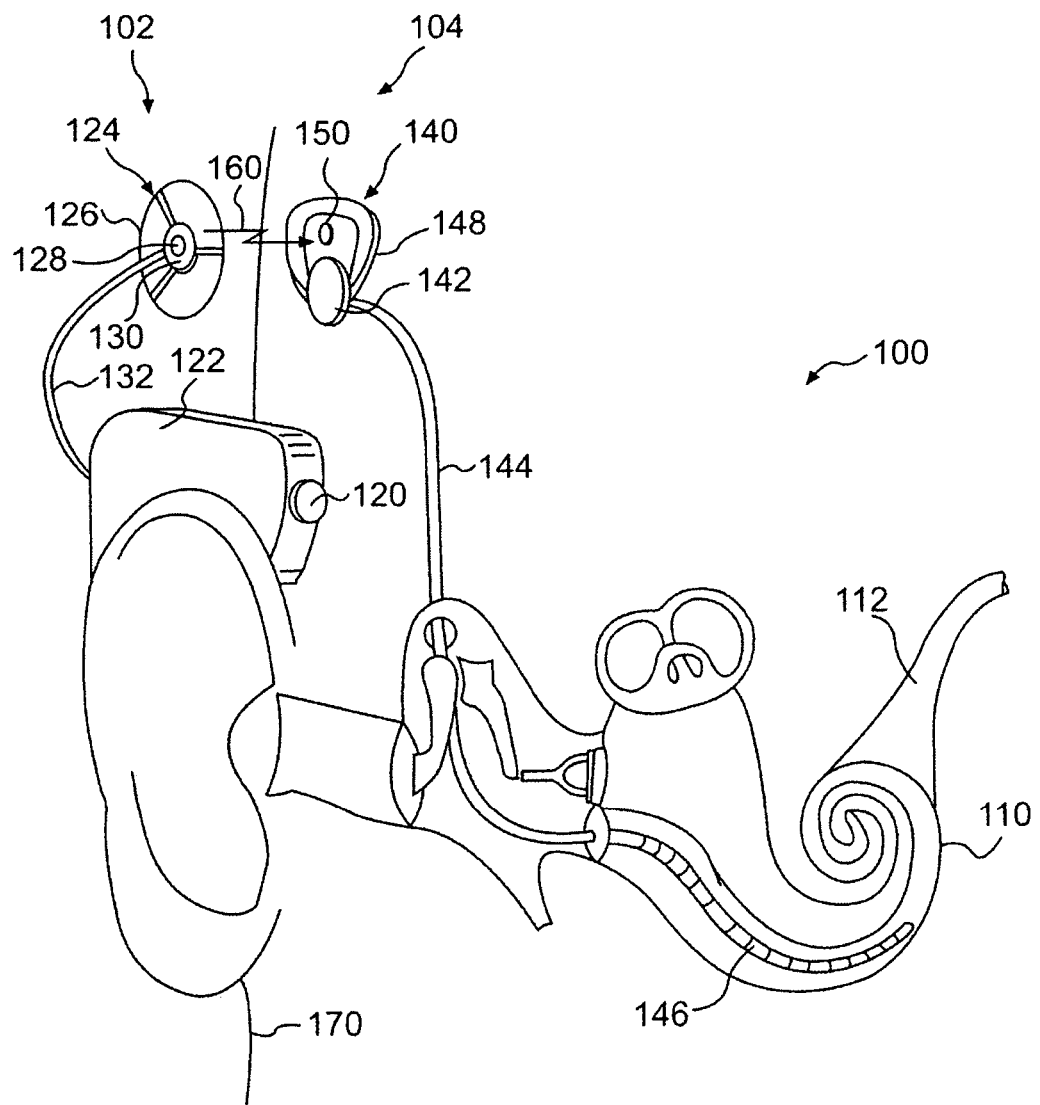
FIG. 1 is a perspective view of an exemplary prosthetic hearing implant system in which embodiments of the present invention may be advantageously implemented.

FIG. 1 is a schematic diagram of an exemplary prosthetic hearing implant system 100 in which embodiments of the present invention may be implemented. Implant system 100 comprises external components 102 which are directly or indirectly attached or secured to the recipient, and internal components 104 which are implanted adjacent to and in the ear 106 of the recipient. For simplicity, ear 106 is shown to comprise a cochlea 110 and an acoustic nerve 112.

External components 102 comprise a microphone 120 for detecting sounds, a speech processor 122 that converts the detected sounds into a coded signal, a power source (not shown), and an external transmitter unit 124. External transmitter unit 124 comprises an external coil 126 and a magnet 128 secured to external coil 108 in housing 130. Speech processor 122 processes the output of microphone 122. Speech processor 122 generates a coded signal which is provided to external transmitter unit 124 via cable 132.

Internal components 104 comprise an internal receiver unit 140, a stimulator unit 142, and an electrode assembly 144 having an electrode array 146. Electrode assembly 144 extends into cochlea 110 and provides the coded signal to the nerve fibers (not shown) through electrode array 146. This stimulates hearing for a recipient with damage to cochlea 110, or surrounding tissue and/or nerves. Internal receiver unit 140 comprises an internal coil 148 and a magnet 150 fixed relative to internal coil 148. Internal coil 148 receives power and data, represented by arrow 160, from external coil 124 through the skin 170 of the recipient.

The efficiency of the transcutaneous link 160 is determined by a number of factors one of which is the extent to which external and internal coils 126, 148 are aligned. That is, as the relative lateral offset between external and internal coils 126, 148 increases, the efficiency of the magnetic coupling of the coils decreases.

In the exemplary embodiments described herein, internal coil 148 is aligned with external coil 124 using magnets 128 and 150. Since the attractive magnetic force between magnet 128 and magnet 150 is not permanent, external transmitter unit 124 may be removed and adjusted. Although magnets 128, 150 provide sufficient coupling strength to hold external coil 126 in alignment with internal coil 148, it is oftentimes desirable to adjust the attractive forces between the internal and external magnets 128, 150 so that the alignment is maintained despite different environmental conditions and recipient activity.

Embodiments of the present invention described below utilize a threaded shaft in the external coil housing and a magnet having reciprocal threads to provide the recipient with the capability of adjusting the attractive force between the magnets as needed or desired. As shown by FIG. 1, external transmitter unit 124, including external coil 126, housing 130 and magnet 128, rests against skin 170 of the recipient and may be in contact with dirt, oil, particles and other debris. Further, the surface of external transmitter unit 124 not resting against skin 170 may be exposed to hair, headwear, etc. (not shown) which covers external transmitter unit 124 and may also contain dirt, oil, particles and other debris. The environment, such as wind, rain, etc., also may be in contact with the exposed surface of external transmitter unit 124. Thus, housing 130 and its magnet 128 are exposed to debris originating from opposing sides of housing 130.

Over repeated and continuous use, the recipient may accumulate debris between housing 130 and magnet 128 which may lead to a decreased performance and comfort of external transmitter unit 124. In addition, such debris may decrease the sanitary environment for implant system 100, especially after surgery in the same location. In particular, the accumulate debris in the space separating housing 130 from magnet 128 may lodge magnet 128, making it difficult to adjust or remove magnet 128 without applying an excessive force. Without the ability to easily adjust or remove magnet 128, the recipient may accidentally crack or break housing 130, external coil 124, or other components of external unit 102 when trying to adjust or remove magnet 128. Replacing or repairing such components is usually more expensive than replacing or fixing magnet 128.

Figure 2A:
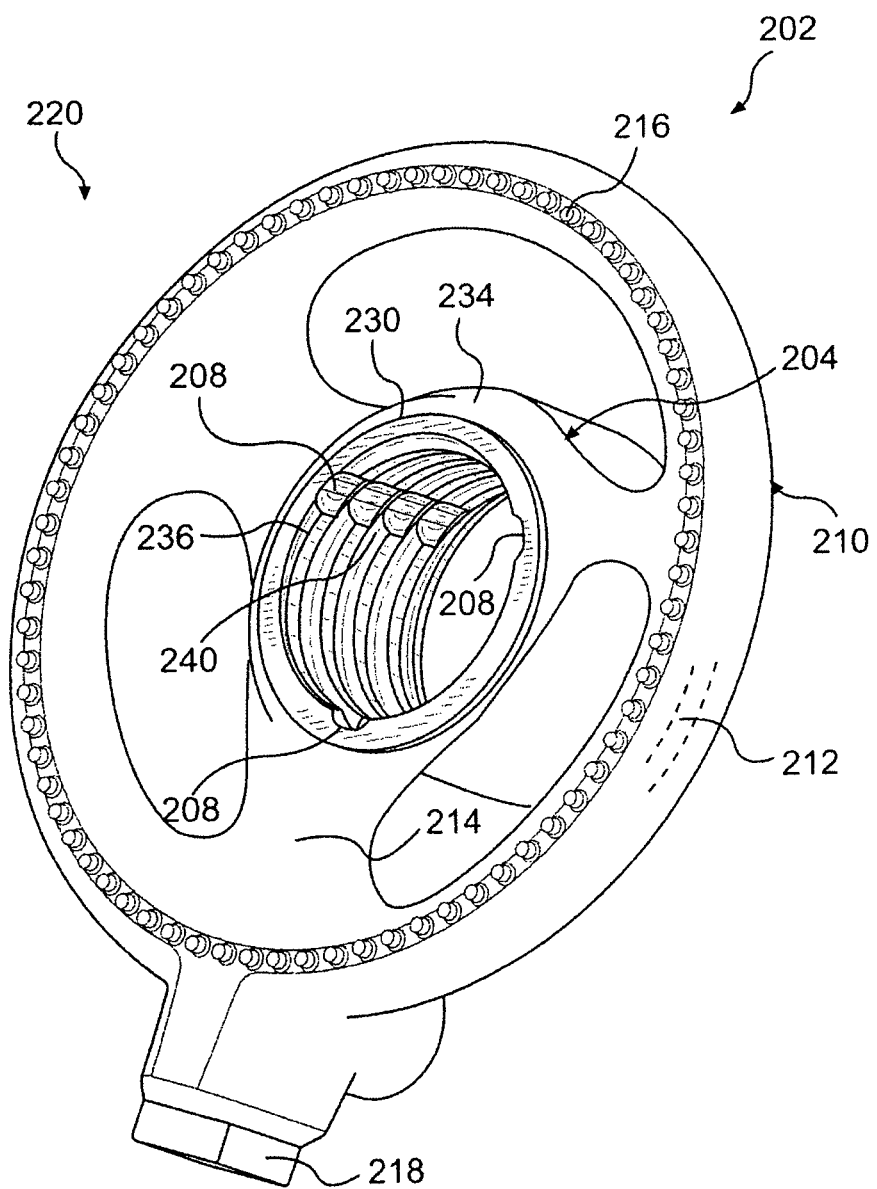
FIG. 2A is a perspective view of a proximal side of an external transmitter unit in accordance with an embodiment of the present invention.
Figure 2B:
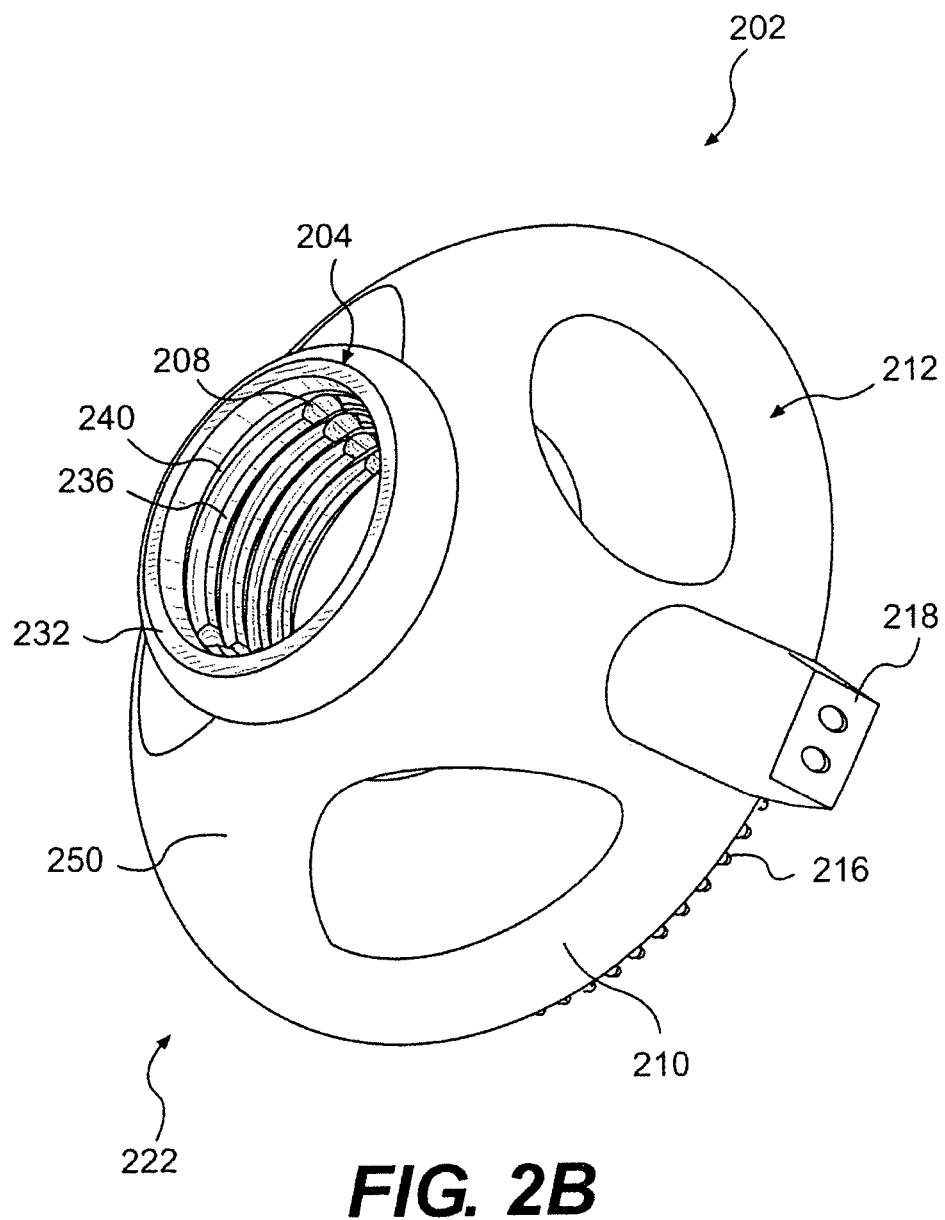
FIG. 2B is a perspective view of one embodiment of a distal side of the external transmitter unit shown in FIG. 2A.
Figure 2C:
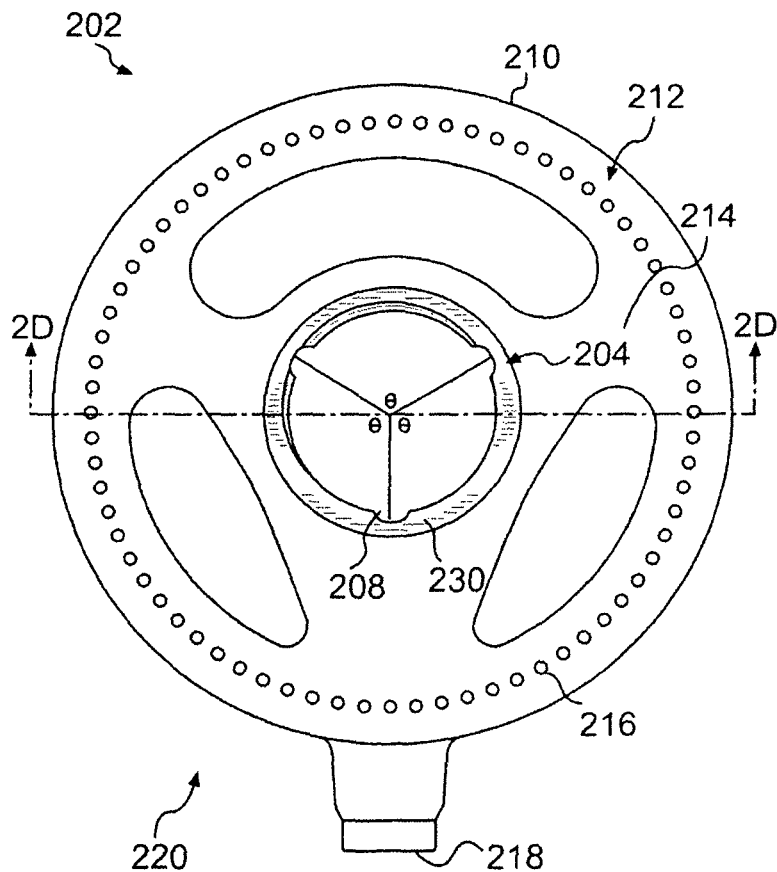
FIG. 2C is a bottom view of one embodiment of the proximal side of the external transmitter unit shown in FIG. 2A.
Figure 2D:
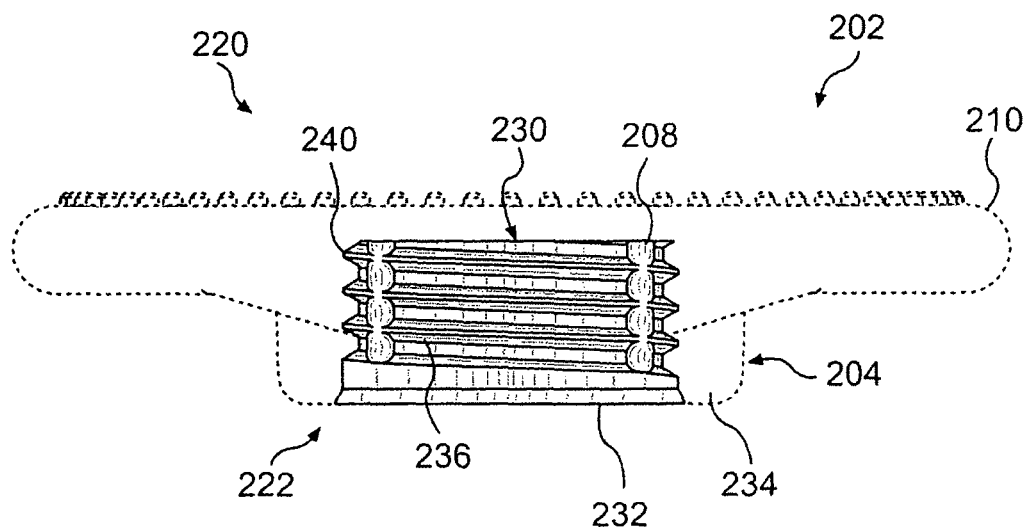
FIG. 2D is a cross-sectional view of one embodiment of the external coil housing shown in FIG. 2C.

Exemplary embodiments of the present invention will be described in detail below with reference to FIGS. 2A-2D. FIG. 2A is a perspective view of a skin-adjacent side of an external coil assembly housing in accordance with one embodiment of the present invention. FIG. 2B is a perspective view of one embodiment of an exposed side of the external coil assembly housing shown in FIG. 2A. FIG. 2C is a bottom view of one embodiment of the skin-adjacent side of the external coil assembly housing shown in FIG. 2A. FIG. 2D is a cross-sectional view of one embodiment of the external coil assembly housing shown in FIG. 2C.

An external coil assembly 220 comprises a housing 202 having a skin-adjacent side 234 and an opposing exposed side. An external coil 212 is secured or otherwise integrated in housing 202. In the exemplary embodiment shown in FIGS. 2A-2D, external coil 212 is located along a peripheral region 210 of housing 202 to define an outer ring of external coil assembly 220. Along peripheral region 210 there are a series of optional dimples 216 adapted to rest against skin 170 of a recipient. External coil assembly 202 is connected to speech processor 122 through cable 132 via port 218.

In a raised interior region of external coil housing 202 there is a shaft 204 having a raised helical rib, or thread 236. In the embodiment shown in FIGS. 2A-2D, threaded shaft 204 terminates at a proximal rim 230 which opens to the skin-adjacent side 234 of housing 202, and terminates at a distal rim 232 which opens to the exposed side of housing 202. As one of ordinary skill in the art would appreciate, threaded shaft 204 may open to only one side of housing 202 to allow for removal of the magnet (not shown), as well as to allow for the recipient to remove debris in the transverse channels 208, as described elsewhere herein.

In the embodiment shown, there are portions of housing 202 which are removed to facilitate ventilation of external coil assembly 220 when in operation on a recipient. This results in the formation of support arms 214 connecting the interior and peripheral regions of housing 202.

At least one transverse channel 208 is formed in thread 236, causing discontinuities in the thread. In the embodiment illustrated in FIGS. 2A-2D, there are three transverse threads 208 radially distributed around shaft 204. As one of ordinary skill in the art would appreciate from the present description, however, any quantity of transverse channels 208 may be implemented depending on a variety of factors such as the anticipated quantity of debris, the mechanical integrity that is to be maintained between the magnet (not shown) and housing 202, etc. Such transverse channels 208 may be located at any absolute or relative position around shaft 204. In one particular embodiment, a plurality of transverse channels 208 are radially distributed in evenly spaced increments around shaft thread 236, as represented by angle θ in FIG. 2C.

Also, in the illustrative embodiment, transverse channels 208 extend substantially parallel to the axis of shaft 204 and, therefore substantially perpendicular to a plane parallel to the helical turns of thread 236. As one of ordinary skill in the art would appreciate, in alternative embodiments, one or more transverse channels 208 may be at any angle relative to the axis of shaft 204 and the helical plane of thread 236 depending on the particular application, performance, environment, and other factors.

Thread 236 defines an inner diameter measured between the apex of opposing portions of the thread, and an outer diameter measured between the base of opposing portions of the thread.

Thread 236 may be a triangle-shaped thread, a square-shaped thread or a trapezoid-shaped thread, or other shape, depending on the particular application and desired accuracy. In respect to thread standards, embodiments of thread 236 may be compliant with metric thread, unified thread and other thread standards now or later developed.

Figure 4A:
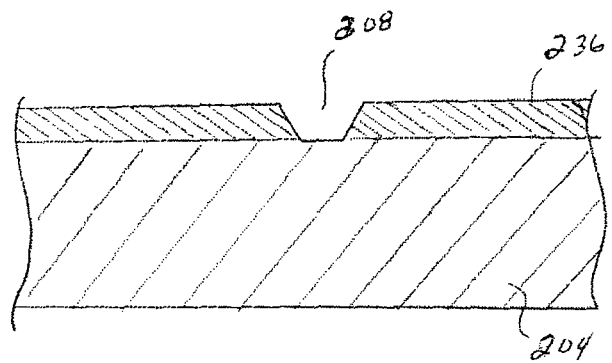
FIG. 4A is a cross-sectional view of a transverse channel in accordance with one embodiment of the present invention.
Figure 4B:
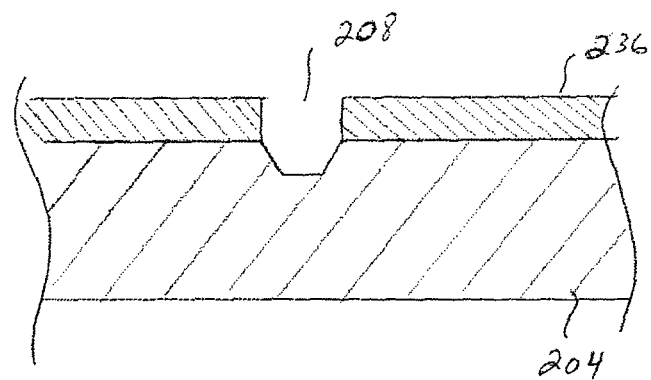
FIG. 4B is a cross-sectional view of a transverse channel in accordance with an alternative embodiment of the present invention.

Transverse channels 208 comprise a bottom wall and opposing side walls as shown in FIGS. 4A and 4B. Transverse channels 208 may have any cross-sectional shape. For example, in one embodiment, the side and bottom walls are planar and substantially orthogonal to each other. In an alternative embodiment, the side and bottom walls are curved to form a U-shaped cross-section. In the embodiments shown in FIGS. 4A and 4B, the planar side walls are at an approximate 60 degree angle with the bottom wall. In addition, the cross-sectional shape of transverse channels 208 may vary or may be the same between a plurality of transverse channels 208.

As noted, in one embodiment, transverse channels 208 create periodic breaks or discontinuities in thread 236. In one embodiment, the side walls are formed by the exposed sides of portions or segments of thread 236 while the bottom wall is formed by the surface of shaft 204 defining the outer diameter of shaft thread 236. A cross-sectional view of such an embodiment is illustrated in FIG. 4A. In an alternative embodiment, one or more of transverse channels 208 is/are recessed in the wall of shaft 204 defining the outer diameter of shaft thread 236. A cross-sectional view of such an embodiment is illustrated in FIG. 4B. It should be appreciated by those of ordinary skill in the art that any combination of transverse channel depth may be implemented among the plurality of transverse channels, and that the transverse channels may have any depth appropriate for a particular application, environment, performance, etc. For example, the dimensions of one or more transverse channels 208 may be configured to accommodate anticipated debris having certain dimensions.

In a further embodiment, channels 208 may extend along a portion or the entire length of shaft 204. In the embodiment shown in FIGS. 2A-2D, channels 208 are open to the exposed and skin-adjacent sides of external coil housing 202. It should be appreciated, however, that transverse channels 208 may not be open to one or both surfaces, and may extend along only a portion of shaft 204. Furthermore, not all transverse channels 208 need to be the same length or open to the same surface of housing 202.

In a further embodiment, transverse channels 208 may be formed by or coated with a material that facilitates the migration of debris along the channels to the opening at the exposed or skin-adjacent surfaces of external coil housing 202.

Figure 3A:
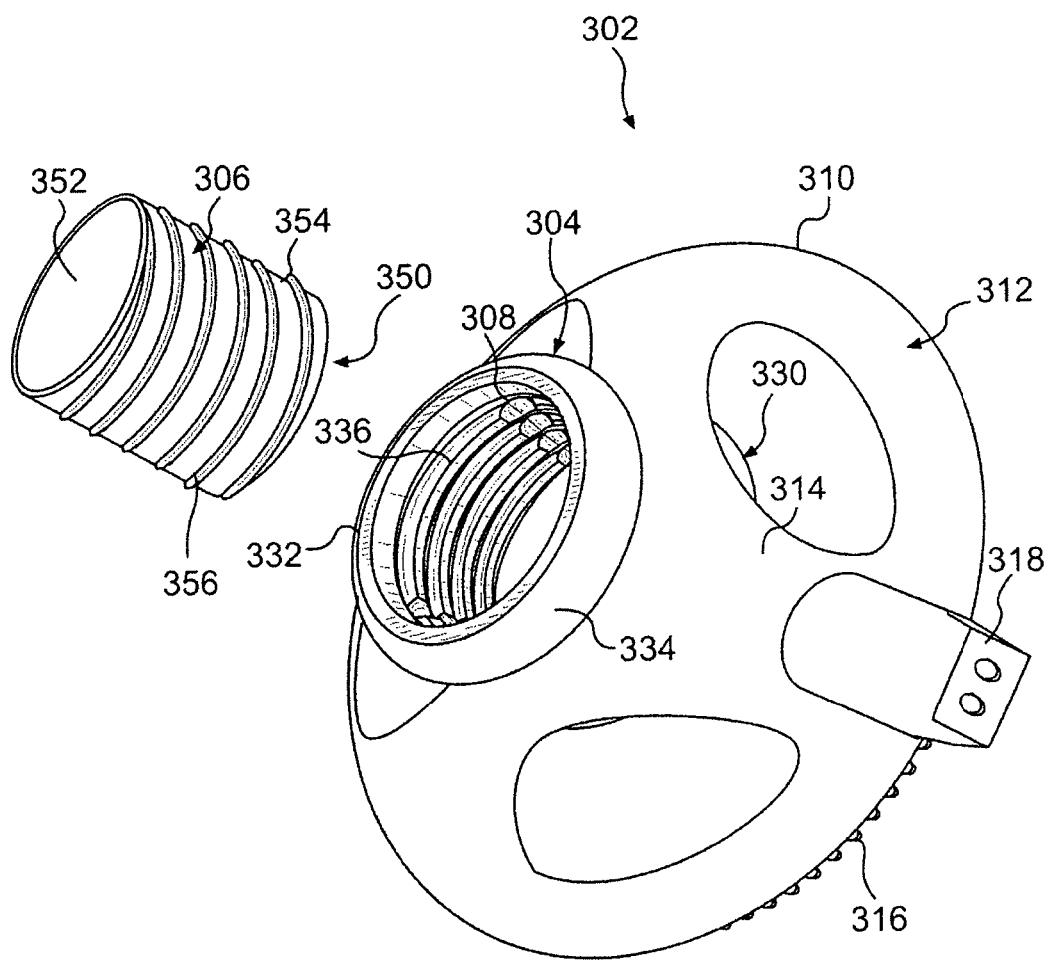
FIG. 3A is a perspective view of one embodiment of an exposed side of an external coil housing with an embodiment of a magnet configured to be inserted into the housing in accordance with an embodiment of the present invention.

In FIG. 3A there is shown a perspective view of external coil housing 302 having a threaded shaft 304 for mating with magnet 306 along with three transverse channels 308 disposed within threaded shaft 304. External coil housing 302 comprises an outer ring 310, having dimples 316, external coil 312 which is connected to housing 304 by support arms 314, and port 318 for connecting external coil housing 302 to a speech processor (not shown). In this embodiment, threaded shaft 304 terminates at a proximal rim 330 and a distal rim 332, and has a cylindrical wall 334 with a thread 336. Extending substantially perpendicular to the axis of shaft 304 are transverse channels 308. A cylindrical magnet 306 has an exterior surface 354 with a thread 356 configured to threadingly engage threaded shaft 304. A proximal end 350 of magnet 306 is inserted into the opening of shaft 304 and rotated to engage threads 256 and 336.

Magnet 306 may be inserted, removed, or adjusted using any suitable technique or tool. For example, means for rotating magnet 306 may be provided at distal end 352, such as a textured surface to facilitate gripping with a finger surface, or a slot to receive a screw driver. These and other known features may be implemented to enable magnet 306 to be threadingly engaged to a desired location in shaft 304.

Figure 3B:
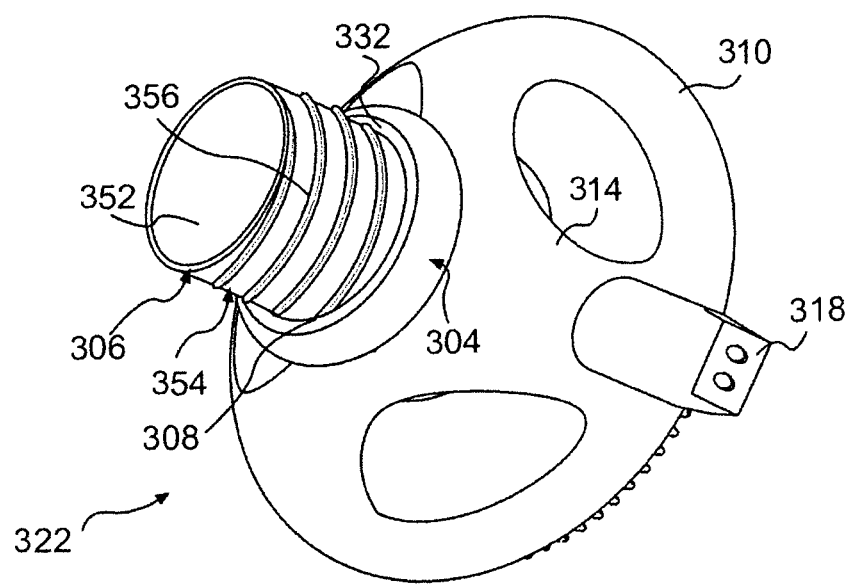
FIG. 3B is a perspective view of one embodiment of the external coil housing with the magnet threadingly engage in the threaded shaft of housing as shown in FIG. 3A.
Figure 3C:
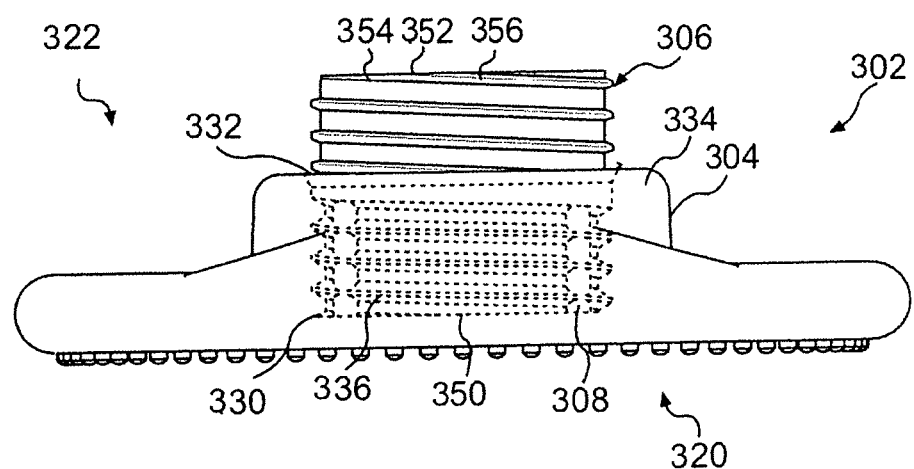
FIG. 3C is a cross-sectional view of one embodiment of the external coil housing shown in FIG. 3B.

Although magnet 306 is shown being inserted, removed or adjusted from a distal side in FIG. 3, the magnet may also be inserted, removed or adjusted from the skin-adjacent side of coil housing 302. In such embodiments, the same or different features may be provided to facilitate such adjustment.

Further, the length of magnet 306 may vary depending on the application, desired attractive force, requirements of the recipient, shape of the external coil housing, etc. In some applications, it may be necessary to use a combination of magnets to obtain the desired coupling of the internal and external coils.

In FIG. 3B magnet 306 is threadingly engaged in shaft 304 such that distal surface 350 is approximately flush with the skin-adjacent surface of exterior coil housing 302. In this embodiment, when magnet 306 is threadingly engaged with shaft 304, transverse channels 308 are accessible within housing 302, even though magnet 306 is present. Further transverse channels 308 maintain a gap between shaft 304 and magnet 306.

An accessible transverse channel 308 provides benefits for the recipient by providing a means for cleaning the mated threads of magnet 306 and shaft 304. Further, channels 308 may allow for the collection of accumulated debris when magnet 306 is inserted, removed or adjusted. The collection of debris provides a "self-cleaning" mechanism, since the rotation of magnet 306 may bias the debris out of an open end of channel 308. Further, once channels 308 collect debris, the recipient may clean the debris by removing the debris from the channels 308.

One advantage of the embodiments of the present invention is that the channels in the housing of the external transmitter do not require a newly designed magnet. Thus, conventional magnets may be used with the embodiments of the present invention without having to obtain specially designed magnets.

Figure 5:
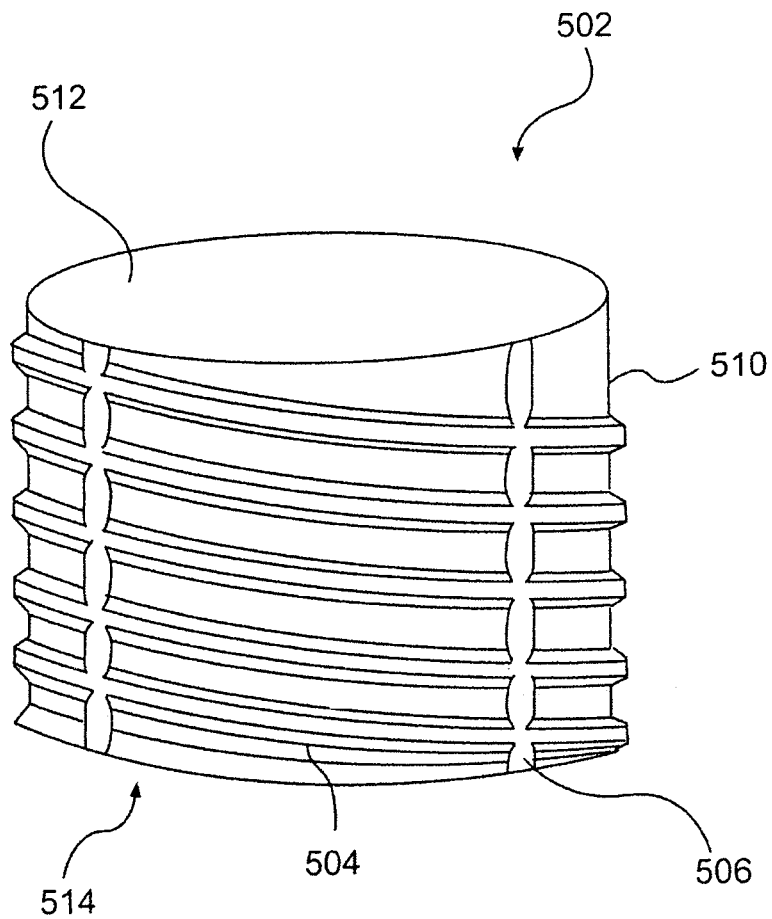
FIG. 5 is a perspective view of a magnet having an exterior thread with transverse channels therein in accordance with an embodiment of the present invention.

FIG. 5 shows an alternative embodiment of the present invention, in which a magnet 502 has transverse channels 504 disposed through thread 506. Thread 506 is on the exterior surface of a cylinder 510 of magnet 502. Transverse channels 504 are substantially perpendicular to the plane of and between the proximal surface 512 and distal surface 514 of magnet 502, although they need not be so in alternative embodiments. Such an embodiment provides similar advantages as the above-described embodiments, and allows magnet 502 to be used with conventional external coils assemblies having a threaded housing.

As one of ordinary skill in the art would appreciate, any and all of the above features of the transverse channels are applicable in and desired combination when the transverse shaft is implemented in magnet 502. It should also be appreciated that in alterative embodiments, any combination of any embodiment of transverse channels may be implemented on both the threaded shaft of the external coil housing and the exterior surface of the corresponding magnet.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An external coil assembly for a transcutaneous system comprising:
    a housing having a skin-adjacent surface, an opposing exposed surface and a threaded shaft open to the exposed surface and extending toward the skin-adjacent surface;
    an external coil secured within the housing; and
    a magnet with a threaded exterior surface to threadingly engage the threaded shaft,
    wherein at least one of either the shaft thread or the magnet thread has at least one transverse channel forming discontinuities in the thread.

2. The assembly of claim 1,
    wherein the transverse channel is substantially perpendicular to the at least one of either the shaft thread or the magnet thread.

3. The assembly of claim 1,
    wherein the shaft thread and the magnet thread are one of either a triangle-shaped, square-shaped and trapezoid-shaped threads.

4. The assembly of claim 1,
    wherein the shaft thread and the magnet thread are configured to be compliant with metric thread standards.

5. The assembly of claim 1,
    wherein the shaft and magnet thread each have an inner diameter and an outer diameter,
    wherein the transverse channel comprises a bottom wall and opposing side walls, and
    wherein the side walls are formed by the threads of the at least one of either the shaft thread or the magnet thread, and the bottom wall is formed by the surface defining the outer diameter of the at least one of either the shaft thread or the magnet thread.

6. The assembly of claim 1,
    wherein the shaft thread and magnet thread each have an inner diameter and an outer diameter,
    wherein the transverse channel comprises a bottom wall and opposing side walls, and
    wherein the transverse channel is recessed in a wall defining the outer diameter of the at least one of either the shaft thread or the magnet thread.

7. The assembly of claim 1, wherein the at least one transverse channel comprises a plurality of transverse channels.

8. The assembly of claim 7, wherein at least some of the plurality of transverse channels are radially distributed around the at least one of either the shaft thread or the magnet thread.

9. The assembly of claim 1,
    wherein the at least one transverse channel opens to the exterior surface of the housing.

10. The assembly of claim 1,
    wherein the threaded shaft and magnet each have a length, and
    wherein the at least one transverse channel extends along substantially the length of one of either the threaded shaft or magnet.

11. The assembly of claim 1,
    wherein the transcutaneous system is an element of a prosthetic hearing implant.

12. The assembly of claim 1,
    wherein the magnet comprises a housing having the magnet threads and an interior configured to retain magnetic material.

13. The assembly of claim 1,
    wherein the skin-adjacent surface comprises a peripheral region adapted to be positioned immediately adjacent to the skin, and a raised interior region adapted to be offset from the skin,
    wherein the threaded shaft is located in the interior region, and
    wherein the at least one transverse channel opens to the skin-adjacent surface.

14. A magnet comprising:
an exterior surface having a thread configured to engage a threaded shaft in an external coil assembly of a transcutaneous system,
wherein the magnet thread has at least one transverse channel forming discontinuities in the thread.

15. The magnet of claim 14, wherein the external coil assembly comprises a housing having a skin-adjacent surface, an opposing exposed surface, and wherein the threaded shaft is open to the exposed surface and extends toward the skin-adjacent surface, and wherein an external coil is located within the housing.

16. The magnet of claim 14,
wherein the transverse channel is substantially perpendicular to the magnet thread.

17. The magnet of claim 14,
wherein the shaft thread and the magnet thread are one of either a triangle-shaped, square-shaped and trapezoid-shaped threads.

18. The magnet of claim 14,
wherein the shaft thread and the magnet thread are configured to be compliant with metric thread standards.

19. The magnet of claim 14,
wherein the magnet thread has an inner diameter and an outer diameter,
wherein the transverse channel comprises a bottom wall and opposing side walls, and
wherein the side walls are formed by the threads of the magnet thread, and the bottom wall is formed by the exterior surface of the magnet that defines the outer diameter of the magnet thread.

20. The magnet of claim 14,
wherein the magnet thread has an inner diameter and an outer diameter,
wherein the transverse channel comprises a bottom wall and opposing side walls, and
wherein the transverse channel is recessed in the exterior wall of the magnet that defines the outer diameter of the magnet thread.

21. The magnet of claim 14, wherein the at least one transverse channel comprises a plurality of transverse channels.

22. The magnet of claim 21, wherein at least some of the plurality of transverse channels are radially distributed around the magnet thread.

23. The magnet of claim 14,
wherein the at least one transverse channel extends to an edge of the exterior surface.

24. The magnet of claim 14,
wherein the magnet has a length, and
wherein the at least one transverse channel extends along substantially the length of the magnet.

25. The magnet of claim 14,
wherein the transcutaneous system is an element of a prosthetic hearing implant.

26. The magnet of claim 14, wherein the magnet further comprises:
a housing comprising the exterior surface having the magnet threads; and
an interior configured to retain magnetic material.

27. An external coil assembly for a transcutaneous system comprising:
housing means for housing an external coil of a transcutaneous system, the housing means having a skin-adjacent surface, an opposing exposed surface and a threaded shaft open to the exposed surface and extending toward the skin-adjacent surface; and
magnet means having a threaded exterior surface for threadingly engaging the threaded shaft,
wherein at least one of either the shaft thread or the magnet thread has at least one transverse channel forming discontinuities in the thread.

28. The assembly of claim 27,
wherein the transverse channel is substantially perpendicular to the at least one of either the shaft thread or the magnet thread.

29. The assembly of claim 27,
wherein the shaft thread and magnet thread each have an inner diameter and an outer diameter,
wherein the transverse channel comprises a bottom wall and opposing side walls, and
wherein the side walls are formed by the threads of the at least one of either the shaft thread or the magnet thread, and the bottom wall is formed by the surface defining the outer diameter of the at least one of either the shaft thread or the magnet thread.

30. The assembly of claim 27,
wherein the shaft and magnet each have an inner diameter and an outer diameter,
wherein the transverse channel comprises a bottom wall and opposing side walls, and
wherein the transverse channel is recessed in a wall defining the outer diameter of the at least one of either the shaft thread or the magnet thread.

31. The assembly of claim 27, wherein the at least one transverse channel comprises a plurality of transverse channels radially distributed around the at least one of either the shaft thread or the magnet thread.

32. The assembly of claim 27, further comprising:
collection means for collecting debris accumulating between neighboring portions of the magnet thread.

* * * * *